(12) United States Patent
Karube et al.

(10) Patent No.: US 10,053,405 B2
(45) Date of Patent: Aug. 21, 2018

(54) METHOD FOR PRODUCING FLUORINE GROUP-CONTAINING HALOOLEFIN COMPOUND AND COMPOSITION

(71) Applicant: DAIKIN INDUSTRIES, LTD., Osaka (JP)

(72) Inventors: Daisuke Karube, Osaka (JP); Masayuki Kishimoto, Osaka (JP); Yuzo Komatsu, Osaka (JP); Takehiro Chaki, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/514,618

(22) PCT Filed: Oct. 7, 2015

(86) PCT No.: PCT/JP2015/078527
§ 371 (c)(1),
(2) Date: Mar. 27, 2017

(87) PCT Pub. No.: WO2016/056602
PCT Pub. Date: Apr. 14, 2016

(65) Prior Publication Data
US 2017/0217860 A1 Aug. 3, 2017

(30) Foreign Application Priority Data
Oct. 7, 2014 (JP) .................................. 2014-206390

(51) Int. Cl.
C07C 17/25 (2006.01)
C07C 17/20 (2006.01)

(52) U.S. Cl.
CPC ............ C07C 17/25 (2013.01); C07C 17/206 (2013.01)

(58) Field of Classification Search
CPC .................................................. C07C 17/206
See application file for complete search history.

(56) References Cited

U.S. PATENT DOCUMENTS

| 6,362,383 | B1 | 3/2002 | Wilmet et al. | |
| 7,795,480 | B2* | 9/2010 | Merkel | C07C 17/206 570/135 |
| 2013/0041190 | A1* | 2/2013 | Pigamo | C01B 7/0712 570/156 |
| 2013/0041191 | A1* | 2/2013 | Pigamo | C01B 7/0712 570/160 |

FOREIGN PATENT DOCUMENTS

| JP | 2002-504528 | 2/2002 |
| JP | 2013-545715 | 12/2013 |
| JP | 2014-503496 | 2/2014 |
| JP | 2014-511349 | 5/2014 |
| WO | 2011/135416 | 11/2011 |
| WO | 2012/066375 | 5/2012 |
| WO | 2012/098420 | 7/2012 |
| WO | 2013/065617 | 5/2013 |
| WO | 2013/067356 | 5/2013 |
| WO | 2014/025065 | 2/2014 |

OTHER PUBLICATIONS

International Search Report dated Dec. 28, 2015 in International (PCT) Application No. PCT/JP2015/078527.
Extended European Search Report dated Feb. 20, 2018 in European Application No. 15848491.5.

* cited by examiner

*Primary Examiner* — Medhanit W Bahta
(74) *Attorney, Agent, or Firm* — Wenderoth, Lind & Ponack, L.L.P.

(57) ABSTRACT

The present invention provides a method for producing a fluorine-containing haloolefin compound, said method being able to reduce the generation of overly fluorinated compounds as by-products in the production of the fluorine-containing haloolefin compound and produce the target product of high purity at a high yield. The invention also provides a halogenated hydrocarbon composition. The method for producing a haloolefin compound through the step of fluorinating a starting material containing at least one of a pentachloropropane or a tetrachloropropene in the presence of a fluorinating agent in a reactor, according to the present invention, includes the step of adding hydrogen chloride to the reactor. The composition according to the present invention contains: at least one member selected from the group consisting of a pentachloropropane and a tetrachloropropene; and hydrogen chloride.

16 Claims, No Drawings

METHOD FOR PRODUCING FLUORINE GROUP-CONTAINING HALOOLEFIN COMPOUND AND COMPOSITION

TECHNICAL FIELD

The present invention relates to a method for producing a fluorine-containing haloalkane that can be used in a refrigerant etc., and also relates to a composition containing a halogenated hydrocarbon and hydrogen chloride.

BACKGROUND ART

Alternative refrigerants such as HFC-125 ($CF_3CHF_2$) and HFC-134a ($CF_3CH_2F$) have been widely used as important replacements for CFC, HCFC, etc., which destroy the ozone layer. However, these alternative refrigerants are potent global warming substances, thus creating concern over the potential effects of their diffusion on global warming. To combat this, these refrigerants are collected after use; however, not all of them can be collected, and their diffusion due to, for example, leakage cannot be ignored. Although the use of $CO_2$ or hydrocarbon-based substances as alternative refrigerants has also been studied, $CO_2$ refrigerants have many difficulties in reducing comprehensive greenhouse gas emissions, including energy consumption, because of the requirement of large equipment due to the low efficiency of the $CO_2$ refrigerants. Hydrocarbon-based substances also have safety problems due to their high flammability.

Fluorine-containing haloolefin compounds with a low warming potential are attracting attention as substances that can solve these problems. As an example of the fluorine-containing haloolefin compounds, 1233xf (2-chloro-3,3,3-trifluoropropene, $CF_3CCl=CH_2$) is known. 1233xf, used alone or in combination with other substances, such as hydrofluorocarbons (HFCs), hydrofluoroolefins (HFOs), and hydrochlorofluoroolefins (HCFOs), is expected to be useful as a refrigerant, and additionally as a blowing agent, propellant, extinguishing agent, or the like. 1233xf is also important as a starting material for producing other hydroolefin compounds such as HFO-1234yf, which is expected to be used for a refrigerant etc., or as a starting material for producing other hydrofluoroolefin precursors such as HCFC-244bb. Various 1233xf production methods are known. A method in which a pentachloropropane, such as 1,1,1,2,3-pentachloropropane (240db), is reacted with hydrogen fluoride (HF) in the presence of a catalyst is known. For example, Patent Literature 1 discloses a technique of producing 1233xf during the process of continuously producing 2,3,3,3-tetrafluoropropene (1234yf) by subjecting 240db to a gas-phase fluorination in the presence of a catalyst.

CITATION LIST

Patent Literature

Patent Literature 1: JP2014-511349A

SUMMARY OF INVENTION

Technical Problem

However, the method for producing a fluorine-containing haloolefin compound by gas-phase fluorination generates overly fluorinated by-products, called "overly fluorinated compounds." It is difficult to produce a desired fluorine-containing haloolefin compound at a high selectivity by the traditional production method, which may also lower the purity or yield. For example, in the case of producing 1233xf having 3 fluorine atoms (the number of fluorine atoms: 3) through gas-phase fluorination, overly fluorinated compounds such as 1234yf having 4 fluorine atoms or 245cb having 5 fluorine atoms (1,1,1,2,2-pentafluoropropane) are generated as by-products. Converting the by-products back into haloolefin compounds having a desired number of fluorine atoms makes the production steps complex, and is also economically disadvantageous. Because of these drawbacks, there has been a demand for production of a high-purity haloolefin compound having a desired number of fluorine atoms at a high yield.

The present invention was made in view of the status quo above. An object of the present invention is to provide a method for producing a fluorine-containing haloolefin compound, said method being able to reduce the generation of overly fluorinated compounds as by-products during the production of the fluorine-containing haloolefin compound and produce the target product of high purity at a high yield. Another object of the invention is to provide a halogenated hydrocarbon composition.

Solution to Problem

The present inventors conducted extensive research to achieve these objects, and found that they can be achieved by performing fluorination in the presence of hydrogen chloride. The present invention was then completed.

Specifically, the present invention relates to the following method for producing a haloolefin compound and composition.

1. A method for producing a fluorine-containing haloolefin compound through the step of fluorinating a starting material containing at least one of a pentachloropropane or a tetrachloropropene in the presence of a fluorinating agent in a reactor,
the method comprising the step of adding hydrogen chloride to the reactor.
2. The method for producing a fluorine-containing haloolefin compound according to Item 1, wherein the fluorinating agent is hydrogen fluoride.
3. The method for producing a fluorine-containing haloolefin compound according to Item 1 or 2, wherein the fluorination is performed in a gas phase.
4. The method according to any one of Items 1 to 3, wherein the pentachloropropane is at least one member selected from the group consisting of 1,1,1,2,3-pentachloropropane and 1,1,2,2,3-pentachloropropane; the tetrachloropropene is at least one member selected from the group consisting of 1,1,2,3-tetrachloropropene and 2,3,3,3-tetrachloropropene; and the fluorine-containing haloolefin compound is 2-chloro-3,3,3-trifluoropropene.
5. The method according to any one of Items 1 to 4, wherein the starting material is at least one member selected from the group consisting of 1,1,1,2,3-pentachloropropane and 1,1,2,2,3-pentachloropropane; and the fluorine-containing haloolefin compound is 2-chloro-3,3,3-trifluoropropene.
6. The method according to any one of Items 1 to 3, wherein the starting material is at least one member selected from the group consisting of 1,1,1,3,3-pentachloropropane and 1,1,3,3-tetrachloropropene; and the fluorine-containing haloolefin compound is 1-chloro-3,3,3-trifluoropropene.

7. The method according to Item 6, wherein the starting material is 1,1,1,3,3-pentachloropropane; and the fluorine-containing haloolefin compound is 1-chloro-3,3,3-trifluoropropene.

8. The method according to any one of Items 1 to 7, wherein the hydrogen chloride is added in an amount of $1 \times 10^{-4}$ to 2 molar equivalents based on the total amount of the pentachloropropane and the tetrachloropropene.

9. The method according to any one of Items 1 to 7, wherein the hydrogen chloride is added in an amount of $1 \times 10^{-2}$ to 1 molar equivalents based on the total amount of the pentachloropropane and the tetrachloropropene.

10. The method according to any one of Items 1 to 7, wherein the hydrogen chloride is added in an amount of $1 \times 10^{-1}$ to 1 molar equivalents based on the total amount of the pentachloropropane and the tetrachloropropene.

11. A composition comprising: at least one member selected from the group consisting of a pentachloropropane and a tetrachloropropene; and hydrogen chloride.

12. The composition according to Item 11, wherein the content of the hydrogen chloride is $1 \times 10^{-4}$ to 2 molar equivalents based on the total amount of the pentachloropropane and the tetrachloropropene.

13. The composition according to Item 11, wherein the content of the hydrogen chloride is $1 \times 10^{-2}$ to 1 molar equivalents based on the total amount of the pentachloropropane and the tetrachloropropene.

14. The composition according to Item 11, wherein the content of the hydrogen chloride is $1 \times 10^{-1}$ to 1 molar equivalents based on the total amount of the pentachloropropane and the tetrachloropropene.

15. The composition according to any one of Items 11 to 14, wherein the pentachloropropane is at least one member selected from the group consisting of 1,1,1,2,3-pentachloropropane, 1,1,2,2,3-pentachloropropane, and 1,1,1,3,3-pentachloropropane; and the tetrachloropropene is at least one member selected from the group consisting of 1,1,2,3-tetrachloropropene and 2,3,3,3-tetrachloropropene.

16. The composition according to any one of Items 11 to 15, wherein the pentachloropropane is at least one member selected from the group consisting of 1,1,1,2,3-pentachloropropane, 1,1,2,2,3-pentachloropropane, and 1,1,1,3,3-pentachloropropane.

Advantageous Effects of Invention

The method for producing a fluorine-containing haloolefin compound according to the present invention comprises the step of adding hydrogen chloride to a reactor in which a starting material is subjected to fluorination. Because of this step, the method can reduce the generation of overly fluorinated compounds as by-products, and can produce a haloolefin compound having a desired number of fluorine atoms of high purity at a high yield.

The composition according to the present invention comprises at least hydrogen chloride. Because of the contained hydrogen chloride, the use of this composition in fluorination can reduce the generation of overly fluorinated compounds as by-products, and can produce a haloolefin compound having a desired number of fluorine atoms of high purity at a high yield.

DESCRIPTION OF EMBODIMENTS

The following describes embodiments of the present invention in detail.

The production method according to this embodiment produces a fluorine-containing haloolefin compound through the step of fluorinating a starting material containing at least one of a pentachloropropane or a tetrachloropropene in the presence of a fluorinating agent in a reactor. In particular, the production method according to this embodiment comprises the step of adding hydrogen chloride to the reactor. Because of this step, the method can reduce the generation of overly fluorinated by-products (i.e., overly fluorinated compounds), and can produce a haloolefin compound having a desired number of fluorine atoms of high purity at a high yield. The production method is particularly advantageous in producing haloolefin compounds having 3 fluorine atoms as substituents (e.g., trifluoropropene compounds, such as 1233xf).

The starting material for use in the production method according to this embodiment is a compound containing at least one of a pentachloropropane or a tetrachloropropene.

The structure of the pentachloropropane is not particularly limited. Any type of isomer can be used, as long as the pentachloropropane is propane containing 5 chlorine atoms as substituents. From the standpoint of further reduced generation of overly fluorinated compounds, the pentachloropropane is preferably 1,1,1,2,3-pentachloropropane (hereinafter, simply referred to as "240db"), 1,1,2,2,3-pentachloropropane (hereinafter, simply referred to as "240aa"), 1,1,1,3,3-pentachloropropane (hereinafter, simply referred to as "240fa"), or the like, and particularly preferably 240db or 240aa.

The structure of the tetrachloropropene is also not particularly limited. Any type of isomer can be used, as long as the tetrachloropropene is propene containing 4 chlorine atoms as substituents. From the standpoint of further reduced generation of overly fluorinated compounds, the tetrachloropropene is preferably 1,1,2,3-tetrachloropropene (hereinafter, simply referred to as "1230xa"), 2,3,3,3-tetrachloropropene (hereinafter, simply referred to as "1230xf"), or 1,1,3,3-tetrachloropropene (hereinafter, simply referred to as "1230za"), and particularly preferably 1230xa or 1230xf.

The starting material may be either a pentachloropropane or a tetrachloropropene, or may be a combination of both. The starting material may be one type of compound, or may be a combination of two or more types of compound. The starting material may contain one or more compounds other than a pentachloropropane and a tetrachloropropene, to such a degree that the effect of the present invention is not impaired. Examples of the compounds other than a pentachloropropane and a tetrachloropropene include propane having a different number of halogen atoms as substituents, hydrocarbons containing no halogen atoms as substituents, and halogenated hydrocarbons having a different number of carbon atoms.

The production method according to this embodiment comprises the step of adding hydrogen chloride to a reactor in which the starting material is subjected to fluorination.

The method for adding hydrogen chloride to the starting material is not particularly limited. For example, the following methods may be used: a method comprising supplying a starting material to a reactor beforehand and further adding hydrogen chloride thereto, or a method comprising supplying a starting material and hydrogen chloride to a reactor simultaneously. Alternatively, hydrogen chloride may be supplied to a reactor beforehand, and then a starting material may be added thereto.

When hydrogen chloride is supplied to a reactor, hydrogen chloride may be supplied from any part of the reactor. For example, when a starting material is continuously supplied from the inlet of a reactor to perform fluorination in the reactor, and the product is continuously discharged from the outlet of the reactor ("continuous reaction mode"), hydrogen chloride is preferably supplied from the inlet of the reactor. When hydrogen chloride is supplied from the inlet of a reactor, the generation of overly fluorinated compounds is likely to be reduced, and a haloolefin compound having 3 fluorine atoms as substituents (e.g., 1233xf) in particular can be efficiently produced. Even in the continuous reaction mode, the order of supplying the starting material and hydrogen chloride is not particularly limited. After the starting material is supplied, hydrogen chloride may be supplied, or both may be supplied to a reactor simultaneously. However, from the standpoint of further reduced generation of overly fluorinated compounds, it is preferable to supply both to the reactor simultaneously.

The amount of hydrogen chloride supplied to a reactor is, for example, $1 \times 10^{-4}$ to 2 molar equivalents based on the total amount of a pentachloropropane and a tetrachloropropene contained in the starting material. When the amount of hydrogen chloride supplied to the reactor falls within this range, the generation of overly fluorinated compounds as by-products is sufficiently reduced, and cumbersome steps are not required in deacidification of the reaction outlet gas. The amount of hydrogen chloride supplied to the reactor is preferably $1 \times 10^{-2}$ to 1 molar equivalents, and particularly preferably $1 \times 10^{-1}$ to 1 molar equivalents based on the total amount of a pentachloropropane and a tetrachloropropene.

Hydrogen chloride is also generated when the starting material is fluorinated. However, the generation of hydrogen chloride occurs in order from the inlet of the reactor or the inlet of the reactive site such as the catalyst layer. Unless hydrogen chloride is separately supplied to the reactor as described above, hydrogen chloride becomes almost absent around the inlet of the reactor, facilitating the excessive fluorination of the product around the inlet. This means that the hydrogen chloride generated during fluorination of the starting material is unlikely to contribute to reduction of overly fluorinated compounds.

The fluorination of a pentachloropropane or a tetrachloropropene contained in the starting material may be performed with a fluorinating agent either in the presence of a catalyst, or in the absence of a catalyst.

The fluorinating agent for use is preferably hydrogen fluoride. When fluorination is performed in the presence of a catalyst, the type of the catalyst is not particularly limited. Catalysts traditionally used in fluorination of halogenated hydrocarbons can be used. For example, known materials traditionally used in this reaction as a catalyst can be used. Examples of such materials include halides and oxides of transition metals, the elements of group 14, or the elements of group 15. Before performing fluorination, the reactor may be packed with a catalyst.

Typically, it is suitable that the amount of the fluorinating agent is about 1 to 100 mol per mol of a pentachloropropane and a tetrachloropropene, and the amount of the fluorinating agent may be about 5 to 50 mol per mol of a pentachloropropane and a tetrachloropropene.

When the fluorinating agent, or pentachloropropane and/or tetrachloropropene is supplied to a reactor, a gas inert to the starting material and the catalyst, such as nitrogen, helium, or argon, may also be present. When the starting material is supplied to a reactor, an oxidizer such as oxygen or chlorine may be supplied together.

The reactor is preferably a tubular reactor. The method for contacting the starting material with the catalyst is preferably a fixed bed technique. The reactor is preferably made from a material resistant to the corrosive action of hydrogen fluoride.

The reaction may be performed in either a liquid phase or gas phase, and is preferably performed in a gas phase. In the use of a gas phase, hydrogen chloride can reduce the generation of overly fluorinated compounds to a particularly greater degree.

The reaction temperature in the fluorination is not particularly limited, and is typically about 200° C. to 550° C. The pressure in the fluorination is also not particularly limited, and the reaction can be performed under reduced pressure, normal pressure, or increased pressure. Typically, the reaction is performed under a pressure in the vicinity of atmospheric pressure (0.1 MPa). However, the reaction can be smoothly performed, even under a reduced pressure of less than 0.1 MPa. The reaction can also be performed under an increased pressure, unless the increased pressure liquefies the starting material.

There is no limitation on the reaction time. When a catalyst is used, the contact time represented by W/F, i.e., the ratio of the amount of packed catalyst W (g) to the total flow rate F0 (a flow rate at 0° C. and 0.1 MPa: cc/sec) of gas components supplied to the reaction system, is preferably about 0.1 to 90 g·sec/cc, and more preferably about 1 to 50 g·sec/cc. When a catalyst is not used, the contact time represented by V/F, i.e., the ratio of the volume of the reactor V (cc) to the total flow rate F0 (a flow rate at 0° C. and 0.1 MPa: cc/sec) of gas components supplied to the reaction system, is preferably about 0.1 to 100 sec, and more preferably about 1 to 30 sec. The total flow rate of gas components as used herein means the total flow rate of the starting material, hydrogen fluoride, and hydrogen chloride, with optionally used inert gas, oxygen, etc.

The fluorination generates a trifluoropropene. The structure of the trifluoropropene varies depending on the type of tetrachloropropene (HCO-1230) or pentachloropropane (HCC-240) contained in the starting material. For example, when the starting material is 240db, 240aa, 1230xa, or 1230xf described above, the product of the fluorination is 1233xf (2-chloro-3,3,3-trifluoropropene, $CF_3CCl=CH_2$) in every case. When the starting material is 240fa or 1230za described above, the product of the fluorination is 1233zd (1-chloro-3,3,3-trifluoropropene, $CF_3CH=CHCl$) in both cases.

Because the production method according to this embodiment comprises the step of adding hydrogen chloride to a reactor in which the starting material is subjected to fluorination, the method reduces the generation of overly fluorinated compounds as by-products. Thus, haloolefin compounds having 3 fluorine atoms as substituents, such as 1233xf and 1233zd, are produced at a high yield. If fluorination is performed without the step of adding hydrogen chloride to the reactor in which the starting material is subjected to fluorination, haloolefin compounds having more than 3 fluorine atoms as substituents are generated as by-products; i.e., overly fluorinated compounds are generated. For example, 2,3,3,3-tetrafluoropropene (1234yf) and 1,3,3,3-tetrafluoropropene (1234ze) are likely to be generated as a by-product. In the production method according to this embodiment, maintaining the selectivity for overly fluorinated compounds at 10% or less enables efficient production of a desired haloolefin compound. It is preferable to maintain the selectivity for overly fluorinated compounds at 5% or less, and particularly preferable to maintain the selectivity for overly fluorinated compounds at 3% or less.

As described above, in the production method according to this embodiment, reducing the generation of overly fluorinated compounds as by-products can enhance the selectivity for the target product obtained from the starting material; i.e., reducing the generation of overly fluorinated compounds as by-products enables the production of a haloolefin compound having a desired number of fluorine atoms of high purity at a high yield.

When a pentachloropropane, such as 240db or 240aa, is used as a starting material, the pentachloropropane is dehydrochlorinated in a reaction tube, thus becoming prone to conversion into a tetrachloropropene. This tetrachloropropene is more susceptible to catalyst degradation than the pentachloropropane. However, because, in the production method in this embodiment, hydrogen chloride is supplied to the reactor in which fluorination is performed as described above, the dehydrochlorination is suppressed owing to chemical equilibrium. Thus, even in the use of a pentachloropropane as a starting material, the conversion of the pentachloropropane into a tetrachloropropene caused by dehydrochlorination is reduced. This lowers the risk of catalyst degradation caused by the tetrachloropropene, further improving the life of the catalyst. From the standpoint of improving the life of the catalyst for use in fluorination, it is preferable to use a pentachloropropane, such as 240db or 240aa, as a starting material.

In the production method described above, hydrogen chloride is supplied to the reactor, and fluorination is performed. However, in an alternative method, fluorination may be performed using a composition that has been formed by adding hydrogen chloride to the starting material beforehand. The following describes the composition for use in this case.

The composition contains at least one member selected from the group consisting of a pentachloropropane and a tetrachloropropene, and hydrogen chloride.

The type of the pentachloropropane is not particularly limited, and at least one member selected from the group consisting of 240db, 240aa, and 240fa can be used. These types of pentachloropropane facilitate the reduction in generation of overly fluorinated compounds during the fluorination of the composition using a fluorination catalyst.

The type of the tetrachloropropene is not particularly limited, and at least one member selected from the group consisting of 1230xa, 1230xf, and 1230za can be used. These types of tetrachloropropene facilitate the reduction in generation of overly fluorinated compounds during the fluorination of the composition using a fluorination catalyst.

Additionally, as described above, from the standpoint of further improved life of the catalyst for use in the fluorination, it is preferable to use a pentachloropropane rather than a tetrachloropropene.

The content of hydrogen chloride may be $1 \times 10^{-4}$ to 2 molar equivalents based on the total amount of a pentachloropropane and a tetrachloropropene contained in the composition. When the amount of hydrogen chloride supplied to the reactor falls within this range, hydrogen chloride can sufficiently reduce the generation of overly fluorinated compounds as by-products, and problems, such as corrosion of containers in storage, are reduced. The content of hydrogen chloride is preferably $1 \times 10^{-2}$ to 1 molar equivalents, and particularly preferably $1 \times 10^{-4}$ to 1 molar equivalents based on the total amount of a pentachloropropane and a tetrachloropropene.

Because of the hydrogen chloride contained in the composition, fluorination using this composition can reduce the generation of overly fluorinated compounds as by-products, and can produce a haloolefin compound having a desired number of fluorine atoms of high purity at a high yield. The use of, in particular, at least one member selected from the group consisting of a pentachloropropane and a tetrachloropropene as a starting material can produce a trifluoropropene, such as 1233xf or 1233zd, at a high selectivity. Thus, the composition is suitable for use as a starting material in the production of a desired trifluoropropene.

EXAMPLES

The following Examples describe the present invention in more detail. However, the present invention is not limited to the embodiments of the Examples.

The following Examples describe the present invention in more detail. However, the present invention is not limited to the embodiments of the Examples.

Example 1

240db (1,1,1,2,3-pentachloropropane), hydrogen chloride, and hydrogen fluoride were continuously supplied to a reaction tube. The amount of the hydrogen chloride supplied to the reactor was 1 molar equivalent based on 240db. The internal temperature of the reactor was 365° C. The contact time was W/F=10 g·sec/cc. The molar ratio of the hydrogen fluoride to 240db was 10. The reactor was packed with a chromium oxide catalyst beforehand, and fluorination was performed in the presence of the chromium oxide catalyst. The fluorination was performed in a gas phase.

In the fluorination, the conversion of the starting material was 100%, with the selectivity for 1233xf being 93%. The selectivity for 1234yf and 245cb, which were overly fluorinated compounds, was 3%.

Example 2

Fluorination was performed in the same manner as in Example 1, except that the amount of hydrogen chloride supplied to the reactor was 0.6 molar equivalents based on 240db.

In the fluorination, the conversion of the starting material was 100%, with the selectivity for 1233xf being 90%. The selectivity for 1234yf and 245cb, which were overly fluorinated compounds, was 6%.

Comparative Example 1

Fluorination was performed in the same manner as in Example 1, except that hydrogen chloride was not supplied to the reactor.

In the fluorination, the conversion of the starting material was 100%, with the selectivity for 1233xf being 85%. The selectivity for 1234yf and 245cb was as high as 11%. This indicates that the amount of generated 1234yf and 245cb was almost double the amount in Example 2, and that the generation of overly fluorinated compounds was not reduced.

The invention claimed is:

1. A method for producing a fluorine-containing haloolefin compound through the step of fluorinating a starting material containing at least one of a pentachloropropane or a tetrachloropropene in the presence of a fluorinating agent in a reactor, the method comprising the step of adding hydrogen chloride to the reactor, wherein the fluorination is performed in a gas phase, wherein the selectivity for haloolefin compounds having more than 3 fluorine atoms as substituents is 10% or less.

2. The method for producing a fluorine-containing haloolefin compound according to claim 1, wherein the fluorinating agent is hydrogen fluoride.

3. The method according to claim 1, wherein the pentachloropropane is at least one member selected from the group consisting of 1,1,1,2,3-pentachloropropane and 1,1,2,2,3-pentachloropropane; the tetrachloropropene is at least one member selected from the group consisting of 1,1,2,3-tetrachloropropene and 2,3,3,3-tetrachloropropene; and the fluorine-containing haloolefin compound is 2-chloro-3,3,3-trifluoropropene.

4. The method according to claim 1, wherein the starting material is at least one member selected from the group consisting of 1,1,1,2,3-pentachloropropane and 1,1,2,2,3-pentachloropropane; and the fluorine-containing haloolefin compound is 2-chloro-3,3,3-trifluoropropene.

5. The method according to claim 1, wherein the starting material is at least one member selected from the group consisting of 1,1,1,3,3-pentachloropropane and 1,1,3,3-tetrachloropropene; and the fluorine-containing haloolefin compound is 1-chloro-3,3,3-trifluoropropene.

6. The method according to claim 5, wherein the starting material is 1,1,1,3,3-pentachloropropane; and the fluorine-containing haloolefin compound is 1-chloro-3,3,3-trifluoropropene.

7. The method according to claim 1, wherein the hydrogen chloride is added in an amount of $1\times10^{-4}$ to 2 molar equivalents based on the total amount of the pentachloropropane and the tetrachloropropene.

8. The method according to claim 1, wherein the hydrogen chloride is added in an amount of $1\times10^{-2}$ to 1 molar equivalents based on the total amount of the pentachloropropane and the tetrachloropropene.

9. The method according to claim 1, wherein the hydrogen chloride is added in an amount of $1\times10^{-1}$ to 1 molar equivalents based on the total amount of the pentachloropropane and the tetrachloropropene.

10. A composition comprising: at least one member selected from the group consisting of a pentachloropropane and a tetrachloropropene; and hydrogen chloride, wherein the content of the hydrogen chloride is $1\times10^{-4}$ to 2 molar equivalents based on the total amount of the pentachloropropane and the tetrachloropropene.

11. The composition according to claim 10, wherein the content of the hydrogen chloride is $1\times10^{-2}$ to 1 molar equivalents based on the total amount of the pentachloropropane and the tetrachloropropene.

12. The composition according to claim 10, wherein the content of the hydrogen chloride is $1\times10^{-1}$ to 1 molar equivalents based on the total amount of the pentachloropropane and the tetrachloropropene.

13. The composition according to claim 10, wherein the pentachloropropane is at least one member selected from the group consisting of 1,1,1,2,3-pentachloropropane, 1,1,2,2,3-pentachloropropane, and 1,1,1,3,3-pentachloropropane; and the tetrachloropropene is at least one member selected from the group consisting of 1,1,2,3-tetrachloropropene and 2,3,3,3-tetrachloropropene.

14. The composition according to claim 10, wherein the pentachloropropane is at least one member selected from the group consisting of 1,1,1,2,3-pentachloropropane, 1,1,2,2,3-pentachloropropane, and 1,1,1,3,3-pentachloropropane.

15. The method according to claim 1, wherein the selectivity for haloolefin compounds having more than 3 fluorine atoms as substituents is 5% or less.

16. The method according to claim 1, wherein the selectivity for haloolefin compounds having more than 3 fluorine atoms as substituents is 3% or less.

* * * * *